United States Patent
Knee et al.

(10) Patent No.: US 9,005,178 B2
(45) Date of Patent: Apr. 14, 2015

(54) DISPENSING CARTRIDGE

(75) Inventors: Michael Knee, Peiβenberg (DE); Dirk Mueller, München (DE); Ingo W. Wagner, Woerthsee (DE)

(73) Assignee: 3M Innovative Properties Company, Saint Paul, MN (US)

( * ) Notice: Subject to any disclaimer, the term of this patent is extended or adjusted under 35 U.S.C. 154(b) by 1395 days.

(21) Appl. No.: 12/262,961

(22) Filed: Oct. 31, 2008

(65) Prior Publication Data

US 2009/0057338 A1    Mar. 5, 2009

Related U.S. Application Data

(62) Division of application No. 10/867,060, filed on Jun. 14, 2004, now abandoned.

(30) Foreign Application Priority Data

Jun. 18, 2003  (EP) ..................... 03013831

(51) Int. Cl.
  *A61B 19/00*  (2006.01)
  *A61C 5/06*  (2006.01)
  *A61C 9/00*  (2006.01)
  *B65D 81/32*  (2006.01)

(52) U.S. Cl.
  CPC .............. *A61C 5/064* (2013.01); *A61C 5/062* (2013.01); *A61C 5/066* (2013.01); *A61C 9/0026* (2013.01); *B65D 81/3205* (2013.01)

(58) Field of Classification Search
  CPC ........... A61M 5/24; A61M 5/284; A61J 1/06; A61J 1/062; A61J 1/065; A61J 1/10; A61J 1/12; A61C 5/062; A61C 5/064; A61C 5/066; A61C 5/068; A61C 9/0026
  USPC ................. 604/218, 6.11, 207, 414, 403, 208
  See application file for complete search history.

(56) References Cited

U.S. PATENT DOCUMENTS

| | | | | |
|---|---|---|---|---|
| 3,749,021 A * | 7/1973 | Burgess | ......................... | 102/467 |
| 3,767,085 A | 10/1973 | Cannon et al. | .................... | 222/82 |
| 3,817,427 A * | 6/1974 | Neff et al. | ...................... | 222/107 |
| 3,903,886 A | 9/1975 | Omotani | ....................... | 128/218 |
| 4,262,819 A * | 4/1981 | Hayes | .............................. | 222/92 |
| 4,276,830 A | 7/1981 | Pastora | ........................ | 102/467 |
| 4,432,473 A * | 2/1984 | MacEwen | ..................... | 222/327 |
| 4,948,016 A * | 8/1990 | Summons et al. | ............ | 222/158 |
| 5,273,187 A | 12/1993 | Suzuki | ............................ | 222/51 |
| 5,301,835 A * | 4/1994 | Fulks et al. | ...................... | 222/95 |
| 5,330,079 A * | 7/1994 | Keller | ............................. | 222/135 |
| 5,332,122 A * | 7/1994 | Herold et al. | .................. | 222/105 |
| 5,443,182 A * | 8/1995 | Tanaka et al. | .................. | 222/137 |
| 5,585,070 A | 12/1996 | Lessard et al. | ................ | 422/101 |
| 5,593,066 A * | 1/1997 | Konuma et al. | .................. | 222/94 |

(Continued)

FOREIGN PATENT DOCUMENTS

| | | | | |
|---|---|---|---|---|
| DE | 30 01 668 | 7/1981 | ............. | A61M 5/28 |
| EP | 0 413 049 | 2/1991 | ............. | B65D 83/00 |

(Continued)

*Primary Examiner* — Andrew Gilbert
(74) *Attorney, Agent, or Firm* — 3M Innovative Properties Company; Qiang Han

(57) ABSTRACT

A dispensing cartridge, particularly for dental impression materials, formed from a plastic material having at least one inlet and at least one outlet, and including a metal reinforcement tube.

18 Claims, 4 Drawing Sheets

(56) References Cited

U.S. PATENT DOCUMENTS

| | | | |
|---|---|---|---|
| 5,873,492 A | 2/1999 | Sullivan | 722/105 |
| 6,129,244 A * | 10/2000 | Horth | 222/94 |
| 6,158,621 A * | 12/2000 | Keller | 222/95 |
| 6,159,009 A | 12/2000 | Berk et al. | 433/164 |
| 6,311,871 B1 * | 11/2001 | Binder | 222/145.6 |
| 6,631,829 B1 * | 10/2003 | Wagner et al. | 222/23 |
| 6,736,290 B2 * | 5/2004 | Ichikawa et al. | 222/105 |
| 2002/0068257 A1 | 6/2002 | Albach | 433/89 |
| 2002/0190084 A1 | 12/2002 | Ichikawa et al. | 222/327 |
| 2008/0156831 A1 * | 7/2008 | Nakayama et al. | 222/327 |

FOREIGN PATENT DOCUMENTS

| | | | |
|---|---|---|---|
| EP | 0 815 802 | 1/1998 | A61C 5/06 |
| EP | 1266844 | 12/2002 | |
| GB | 2 308 302 | 6/1997 | A61M 5/178 |
| JP | S62-130071 | 8/1987 | |
| JP | H02-28223 * | 2/1990 | |
| JP | 3007390 | 2/1995 | |
| JP | 07163925 | 6/1995 | |
| JP | 11-147982 | 6/1999 | |
| JP | 2001-104854 | 4/2001 | |

* cited by examiner

DISPENSING CARTRIDGE

CROSS REFERENCE TO RELATED APPLICATIONS

This application is a division of U.S. patent application Ser. No. 10/867,060, filed Jun. 14, 2004, now abandoned, which claims priority from EP Application No. 03013831.7, filed Jun. 18, 2003, which are incorporated herein by reference.

FIELD OF THE INVENTION

The present invention relates to a dispensing cartridge, particularly for dental impression materials, of the type adapted to be releasably received in an applicator having a moveable plunger.

BACKGROUND OF THE INVENTION

A number of dispensing devices are available for dispensing various types of materials. In many instances, the dispensing device is an assembly that includes a reusable dispenser or applicator and a disposable cartridge. The cartridge contains a quantity of a composition or material to be dispensed and is releasably received in a receptacle of the applicator.

In one type of dispensing devices, that include an applicator and a cartridge, the applicator has a plunger that is advanced by the user during a dispensing operation. Often, the plunger is received in an open end of the cartridge and bears against a piston within the cartridge. As the plunger is advanced to move the piston, the piston expels a quantity of material through a front outlet opening of the cartridge. The cartridge is made from a plastic material.

Dispensing devices with cartridges are often used in the field of dentistry for mixing and dispensing dental compositions of two components, such as impression materials, restoratives, adhesives, cements, etching gels, sealants and the like. The dispensing cartridge of such devices is made from a plastic material and comprises two compartments which are formed by two cylindrical bodies arranged in parallel to each other. Each compartment contains a specific component, usually a base paste and a catalyst paste. These two components are pressed from their respective compartments out into a mixing tip where the required dental material is prepared. The pressure further urges the mixture out of the mixing tip so that the dental professional can use it as desired.

One type of such dispensing devices is an assembly (e.g., the Garant™ dispenser available from 3M ESPE AG) that includes a reusable, hand-operated applicator and a disposable cartridge (e.g., the cartridge for the polyether impression material Permadyne™ Garant™ available from 3M ESPE AG). The two compartments are of the same cylindrical shape and size and are pre-filled with the two components to be mixed and dispensed.

Another type of such dispensing devices is an automatic dispensing system (e.g., Pentamix™ available from 3M ESPE AG) that includes a motor-driven mixing unit and reusable and interchangeable cartridges (e.g., the cartridge for the polyether impression material Impregum™ Penta™H Duo-Soft, or the cartridge for the polyether impression material Permadyne™ Penta™, or the cartridge for the vinyl polysiloxane impression material Express™ Penta™H, all available from 3M ESPE AG). These two cylindrical compartments have different diameters, and, in use, each accommodates a disposable foil bag pre-filled with the respective component. The larger compartment usually accommodates the foil bag with the base paste. The smaller compartment usually accommodates the foil bag with the catalyst paste. The mixing unit comprises a chamber for holding the cartridge and two parallel motor-driven plungers designed to plunge into the respective compartments and to exert pressure on the components contained in the foil bags.

Both foil bags comprise a respective cap that fits onto the rim of the respective cylindrical body of the dispensing cartridge. The conventional dispensing cartridge is fully made of plastic material which has to be strong enough to stand the pressure applied by the plungers on the bags during use, and which has to be chemically inert to the aggressive, usually acid chemical character of the pastes. Moreover, the plastic material has to be easy to handle in the injection mould, i.e., low shrinking rate and little ability to form shrink marks. These different requirements are difficult to meet.

SUMMARY OF THE INVENTION

In view of the above, the present invention provides a dispensing cartridge, particularly for dental impression materials, with improved stability.

The present invention is directed in one aspect towards a dispensing cartridge, particularly for dental impression materials, for use with an applicator or mixing unit, for example, those having a moveable plunger. The dispensing cartridge according to the present invention is formed of plastic material having at least one inlet and at least one outlet and comprises at least one metal reinforcement tube.

The dispensing cartridge preferably comprises at least one compartment, each comprising a body having an open end for receiving a plunger of an applicator or mixing unit. The body also includes an outlet opening, and the compartment extends between the open end and the outlet opening. Preferably, the metal reinforcement tube is provided within the at least one compartment. It is also preferred that the metal reinforcement tube extends substantially along the entire length of the at least one compartment. The metal reinforcement tube comprises a body having an open end and an outlet opening.

According to a preferred embodiment of the present invention, the outlet opening of the metal reinforcement tube extends beyond the outlet opening of the at least one compartment in the longitudinal direction. Alternatively, the outlet opening of the at least one compartment extends beyond the outlet opening of the metal reinforcement tube in longitudinal direction. If the outlet opening of the metal reinforcement tube extends beyond the outlet opening of the at least one compartment, the dispensing cartridge presents a stepped configuration between the larger outer diameter of the compartment and the smaller outer diameter of the tube. In case the outlet opening of the at least one compartment extends beyond the outlet opening of the metal reinforcement tube, the dispensing cartridge also preferably presents a stepped configuration, with a smaller outer diameter area of the compartment body as the outlet opening of the compartment is approached. Further, alternatively, the outlet opening of the metal reinforcement tube is flush with the outlet opening of the at least one compartment.

The outlet opening of the metal reinforcement tube and/or the outlet opening of the at least one compartment is preferably adapted to releasably receive a cap of a foil bag to be accommodated in the tube. In case the outlet opening of the metal reinforcement tube extends beyond the outlet opening of the at least one compartment, the body of the compartment preferably comprises a longitudinal projection at the face edge thereof in order to provide for a rotational adjustment of the cap on the tube. Alternatively, in case the outlet opening of the compartment extends beyond the outlet opening of the tube, the longitudinal projection is provided in the area of the stepped configuration of the compartment body.

It is preferred that the metal tube extends beyond the compartment. In this case, the cap of the foil bag is received at the outlet opening of the metal tube. This prevents a radial pressure load onto the caps due to the pressurized bag, and thus prevents breaking of the caps.

According to an alternative embodiment, the metal reinforcement tube is closed at the side of the outlet opening with a bottom, said bottom comprising the outlet opening having a diameter smaller than the diameter of the metal reinforcement tube.

Preferably, the open end of the metal reinforcement tube is offset from the open end of the at least one compartment in longitudinal direction so that the open end of the compartment extends beyond the open end of the tube. More preferably, the offset is about 5 to 15 mm, preferably 10 to 13 mm.

According to a preferred embodiment of the present invention, the dispensing cartridge with its at least one compartment is formed by injection moulding. It is preferred that the metal reinforcement tube is held in the at least one compartment in a positively engaging manner. Most preferably, the positive engagement is provided in the area of the open end of the metal reinforcement tube. Due to this positive engagement between the compartment and the tube, there is provided a smooth transition between the plastic part of the dispensing cartridge and the metal part of the cartridge in the interior of the compartment. According to an alternative embodiment, the metal reinforcement tube is fixed within the compartment of the cartridge by means of an adhesive and/or by means of a frictional connection (e.g., a press-fit). In order to provide such a frictional connection, the metal tube comprises a roughened surface, or webs, or indentations.

It is preferred that the open end of the metal reinforcement tube comprises a flared flange or a chamfer. It is also preferred that the open end of the compartment comprises a chamfer or truncated cone. The flared flange or chamfer at the open end of the tube and the chamfer or truncated cone at the open end of the compartment are designed and dimensioned such that there is a smooth transition provided between these two areas in the interior of the cartridge. Preferably, the outmost edge of the flared flange is embedded in the compartment body wall. Thus, the inner diameter of the cartridge, starting from the outmost edge of the compartment/cartridge, decreases as the outlet opening is approached. This facilitates insertion of the plunger during assembly of the cartridge.

Conventional dispensing cartridges also comprised a truncated cone at the open end of the compartment but since the inner core of the injection mould was divided at the transition point where the truncated cone changed to the cylindrical part of the body, at this point, small fins resulting from injection moulding required an after-treatment to remove said fins in order to provide a smooth transition. This problem is overcome with the specific design of the present invention. No after-treatment is required any longer.

According to a preferred embodiment, the dispensing cartridge of the present invention comprises two compartments that are arranged in parallel. Each of these two compartments comprises a metal reinforcement tube as discussed above. Preferably, the two metal reinforcement tubes are identically designed and accommodated within the compartments (for example by positive engagement).

Another aspect of the present invention relates to a method of dispensing a dental composition. The method includes the act of providing a dispensing cartridge being formed of plastic material, and comprising a metal reinforcement tube. The method also includes the act of advancing a plunger in the tube such that a head portion of the plunger urges a dental composition through an outlet opening of the cartridge.

The invention in its various aspects as described is a significant advantage as the metal tubes prevent the cartridge from breaking when overstressed by application forces (e.g., 2000-4000 N) or misuse or by any sort of inadvertent impact. According to a preferred embodiment, the metal reinforcement tubes especially reinforce the rim of the cartridge which is the interface to the caps of the foil bags. Furthermore, the use of a, e.g., stainless metal tube gives an excellent size stability and allows to use plastic materials for the compartment body with better chemical and mechanical characteristics. Moreover, the plastic body can be designed a lot easier in terms of material accumulations.

Further details of the invention are defined in the features of the claims.

DETAILED DESCRIPTION OF THE PREFERRED EMBODIMENTS

Figure 1:
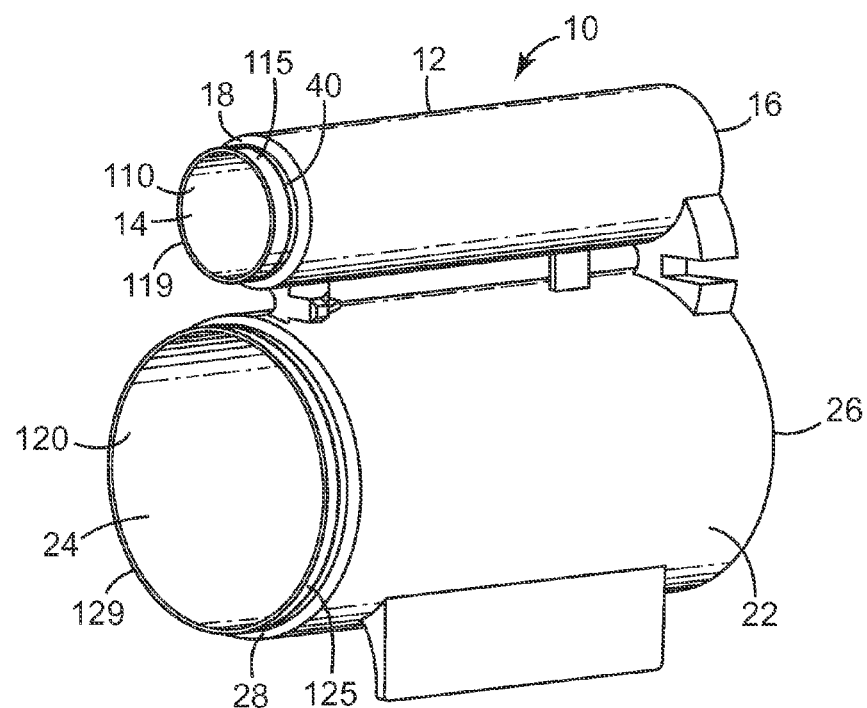
FIG. 1 is a front perspective view of a dispensing cartridge according to one embodiment of the present invention.

An example of a dispensing cartridge constructed in accordance with the principles of the present invention is illustrated in FIG. 1 and is broadly designated by reference numeral 10. The cartridge 10 includes a first compartment with a body 12, having an interior chamber 14. In more detail, the body 12 includes an open end 16 and an outlet or outlet opening 18 that is remote from the open end 16. The compartment is elongated and extends from the open end 16 to the outlet opening 18.

The dispensing cartridge as shown in FIG. 1 comprises a second compartment having a body 22 with interior chamber 24. The body 22 includes an open end 26 and an outlet or outlet opening 28 that is remote from the open end 26. The second compartment is elongated and extends from the open end 26 to the outlet opening 28.

In the shown embodiment, both compartments comprise a metal reinforcement tube, i.e. tubes 110 and 120. The outer diameters of the metal reinforcement tubes 110 and 120 are approximately identical to the inner diameters of the compartments so that the tubes can be accommodated within the compartments. The tubes, for example, can be fixed to the compartments by means of an adhesive or by means of a frictional connection. However, in the shown preferred embodiment the tubes are positively engaged by the compartments being formed by injection moulding from a plastic material. This aspect is described below in more detail.

Figure 7:
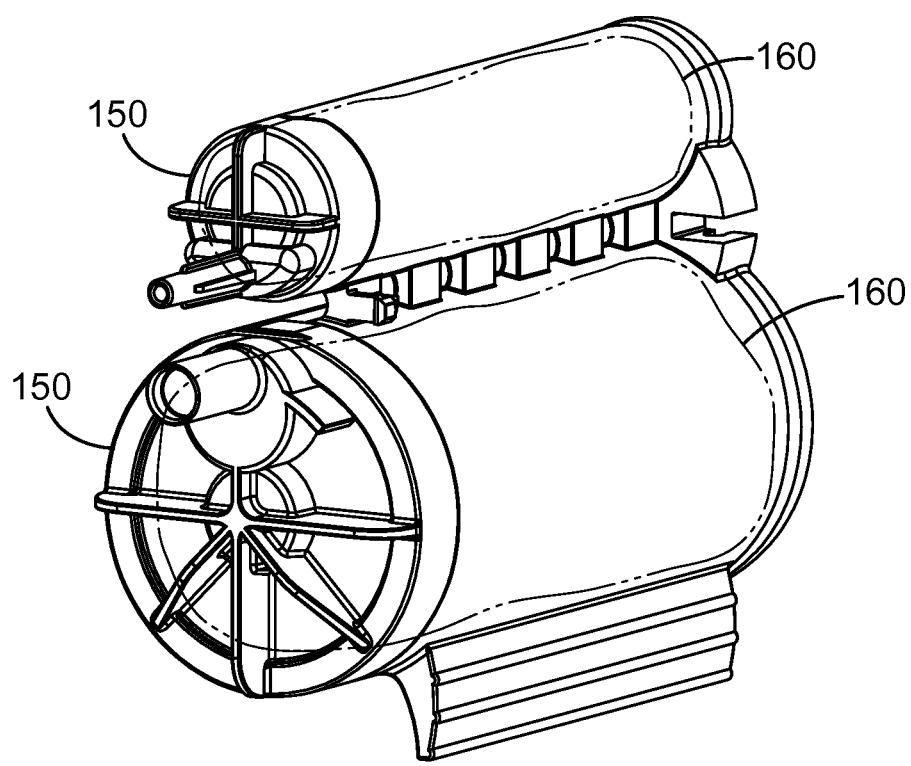
FIG. 7 shows a front perspective view of a dispensing cartridge according to one embodiment of the present invention.

As can be seen in FIG. 1, the outlet openings 119, 129 of the metal reinforcement tubes extend a certain length 115, 125 beyond the outlet openings 18, 28 of the compartments. The tubes are sized such that a foil bag 160 (FIG. 7) filled with the material to be dispensed can be accommodated within the tubes, and caps of the foil bags (not shown) are releasably received on the outlet openings of the tubes. Preferably, the caps of the foil bags comprise a circumferential collar that fits onto the outlet openings of the tubes. In order to provide for a rotational adjustment of the cap on the tubes, each compartment comprises a longitudinal projection, like projection 40 formed at body 12 of the first compartment. Alternatively, a radial projection is provided. Alternatively, a projection in both radial and longitudinal directions is provided.

As shown in FIG. 1, the two compartments of the dispensing cartridge can be arranged substantially in parallel to each other.

Figure 2:
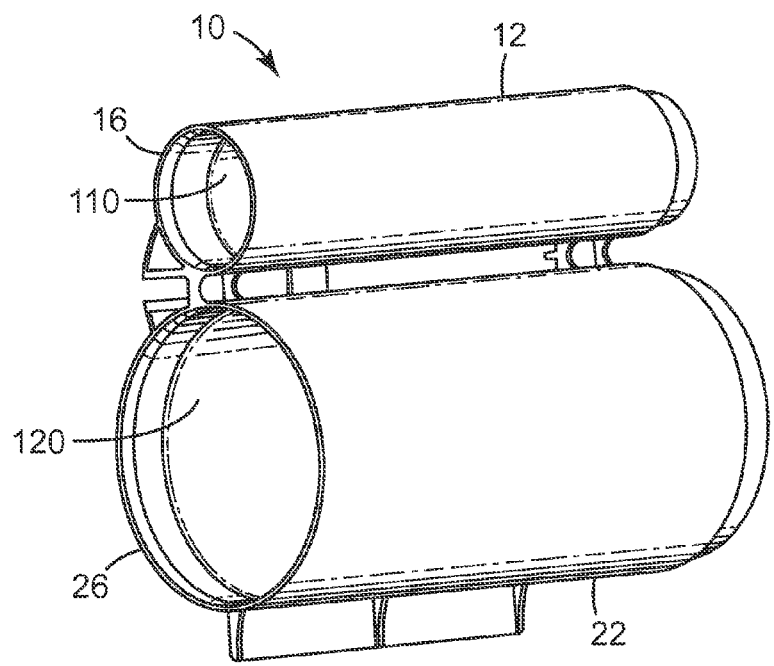
FIG. 2 is a rear perspective view of a dispensing cartridge according to one embodiment of the present invention.

FIG. 2 shows a rear perspective view of the dispensing cartridge 10 according to the preferred embodiment of the present invention. FIG. 2 clearly shows how the metal reinforcement tubes 110, 120 are offset at their open ends from the open ends 16, 26 of the two compartments. Preferably, the open ends of the compartments extend in longitudinal direction beyond the open ends of the tubes, preferably by 5 to 15 mm, more preferably by 10 to 13 mm.

Figure 3:
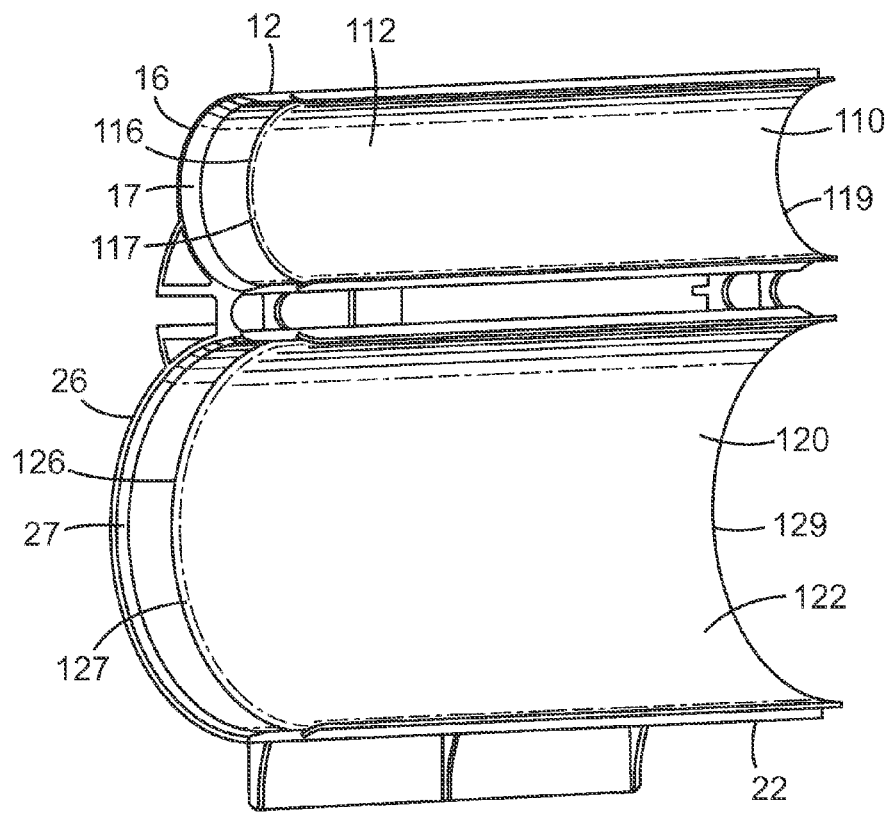
FIG. 3 is a rear cross-sectional perspective view of a dispensing cartridge according to one embodiment of the present invention.

In the present preferred embodiment as shown in FIG. 3, the open ends 16, 26 of the compartments each comprise a chamfer or truncated cone 17, 27, so that the inner diameter of the compartments decrease from the outmost edge of the compartments towards the interior of the compartments. This facilitates insertion of the plungers of the mixing unit. Moreover, in the present preferred embodiment, the open ends 116, 126 of the metal reinforcement tubes each comprise a flared flange or chamfer 117, 127, in order to further facilitate insertion of the plungers of the mixing unit.

Figure 4:
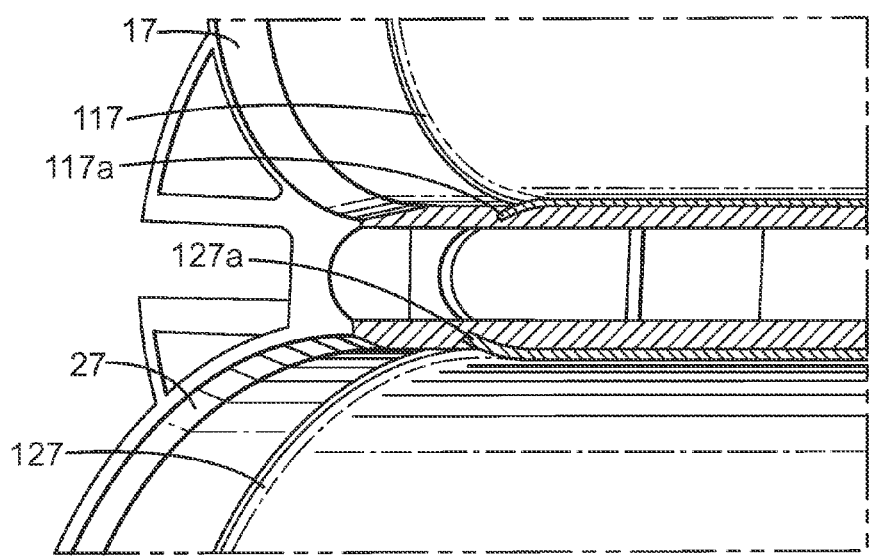
FIG. 4 is a partial rear cross-sectional perspective view of a dispensing cartridge according to one embodiment of the present invention.

As shown in the detailed partial cross-sectional perspective view of FIG. 4, the flared flange or chamfer of the open end 116, 126 of each metal reinforcement tube is positively engaged by the respective body 12, 22 of the surrounding compartment. As can be seen in FIG. 4, the outmost edges 117a, 127a, of the metal reinforcement tubes extend into the plastic compartment bodies, which is achieved during the injection moulding of the compartments with the metal tubes being placed in the injection mould. Such a flared flange or chamfer at the open end of each metal tubes that is embedded in the wall of the respective compartment provides a smooth transition from the inner wall of the compartments to the inner wall of the metal tubes so that the plunger of the mixing unit can easily be moved towards the outlet opening of the tube. Furthermore, no after-treatment at this transition point is necessary, as described above.

Figure 5:
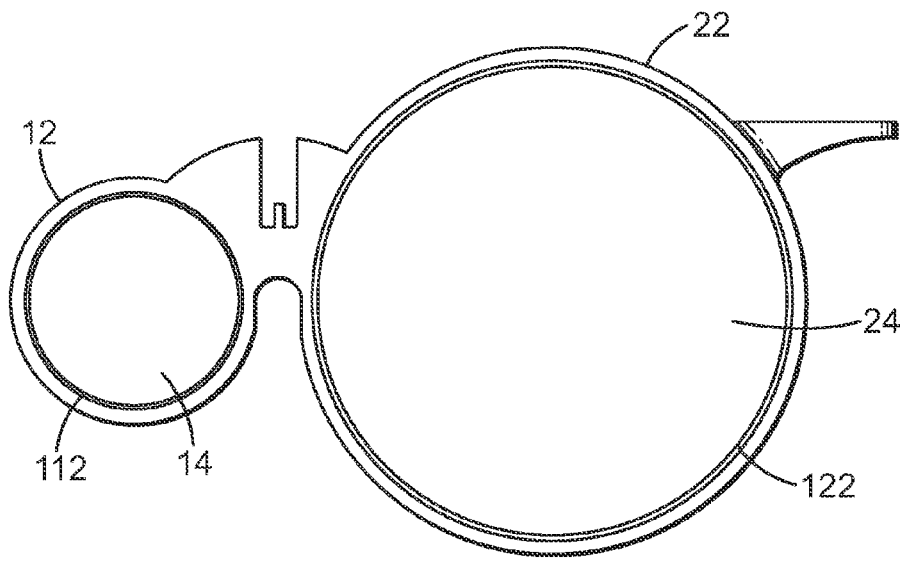
FIG. 5 is a transversal cross-sectional view of a dispensing cartridge according to one embodiment of the present invention.

Finally, FIG. 5 shows a transverse cross-sectional view of the preferred dispensing cartridge with the two metal reinforcement tubes 112, 122 accommodated in the compartment bodies 12, 22.

The caps (shown in FIG. 7 at 150) each comprise a discharge nozzle, and the two discharge nozzles of the two caps 150 are combined by a mixing tip. Thus, upon application of a sufficient force on the foil bags by means of the plungers of the mixing unit, the material contained in the foil bags is discharged through the respective discharge nozzle and mixed in the mixing tip. In case of dental impression materials, the mixed material is discharged by the mixing tip on a dental spoon or into a suitable syringe.

Figure 6:
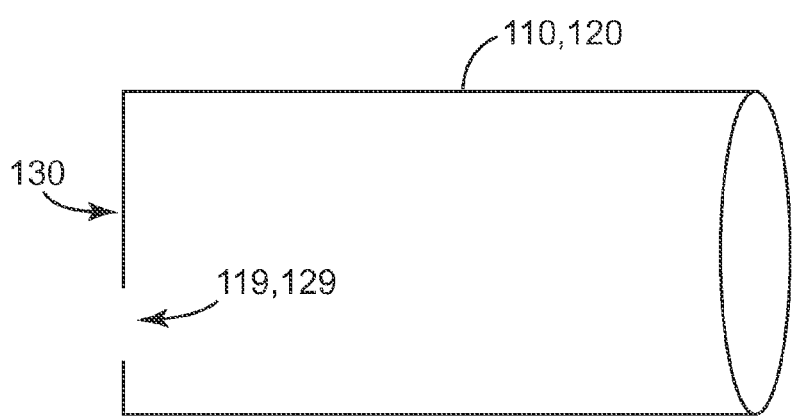
FIG. 6 shows an alternative design of the metal reinforcement tube.

According to an alternative embodiment (see FIG. 6), the metal reinforcement tube 110, 120 is closed at the side of the outlet opening 119, 129 with a bottom 130, said bottom comprising the outlet opening 119, 129 having a diameter smaller than the diameter of the metal reinforcement tube.

Due to the fact that the outlet openings 119, 129 of the metal reinforcement tubes 110, 120 extend beyond the outlet openings 18, 28 of the bodies 12, 22, a stepped configuration is provided. The stepped configuration advantageously enables the dispensing cartridge to be used with conventional applicators and conventional foil bag-cap combinations used with conventional dispensing cartridges. In other words, the dispensing cartridge of the present invention with its plastic compartment and the metal reinforcement tube is designed and dimensioned like a conventional dispensing cartridge. By comparison, simply increasing the thickness of the plastic compartment of conventional cartridges in order to increase the strength would not be as advantageous as the present invention, since the resulting reduced internal diameter or increased outer diameter of such a cartridge would require that foil bags with accordingly reduced outer diameter need to be provided and/or the user would be essentially required to purchase a new mixing unit having a plunger with a smaller diameter and/or the mixing unit needs to be adapted to fit to the increased outer diameter of the cartridge, respectively. Thus, with the present invention, the dispensing cartridge 10 may be used with the relatively expensive mixing units that are already available in the dental office and in the market place.

The cartridge 10 of the present invention is particularly useful for dispensing dental impression materials. However, the cartridge 10 may also be used to dispense non-dental compositions such as adhesives (two- or multi-component adhesives) or other materials for household, industrial, medical or other applications.

Those skilled in the art may recognize that various additions and modifications may be made to the presently preferred embodiments that are described in detail above without departing from the spirit of the invention. As a result, the invention should not be deemed limited to the specific embodiments that are set out, but limited only by a fair scope of the claims that follow along their equivalents.

The invention claimed is:

1. In combination:
   (a) a dispensing cartridge for containing components, the dispensing cartridge adapted to be releasably received by an applicator or a mixing unit for mixing the components, the dispensing cartridge comprising first and second adjoining cylindrical bodies, each cylindrical body having a compartment with at least one inlet and at least one outlet, wherein each compartment has an open end and an outlet opening, and a metal reinforcement tube integrally molded into the cylindrical body of at least one of the compartments to reinforce the respective compartment, wherein the metal reinforcement tube comprises a body having an open end and an outlet opening, wherein the open end of the metal reinforcement tube is offset from the open end of the respective compartment so that the open end of the respective compartment extends beyond the open end of the metal reinforcement tube in a longitudinal direction, and wherein the outlet opening of the metal reinforcement tube extends beyond the outlet opening of at least one of the compartments in the longitudinal direction; and
   (b) a bag containing the component to be dispensed and adapted to be accommodated in the respective compartment having the metal reinforcement tube.

2. The combination according to claim 1, wherein the open end of the metal reinforcement tube comprises a flared flange.

3. The combination according to claim 1, wherein the open end of the metal reinforcement tube comprises a chamfer.

4. The combination according to claim 1, wherein the first and second compartments are each adapted to receive a plunger of an applicator.

5. The combination according to claim 4, wherein the open end of at least one of the compartments comprises a chamfer or a truncated cone.

6. The combination according to claim 1, comprising a smooth transition between the open end of at least one of the compartments and the open end of the metal reinforcement tube.

7. The combination according to claim 1, wherein the metal reinforcement tube is positively engaged at the open end thereof.

8. The combination according to claim 1, wherein the offset is about 5 to 15 mm.

9. The combination according to claim 1, wherein the offset is about 10 to 13 mm.

10. The combination according to claim 1, wherein the outlet opening of the metal reinforcement tube or outlet opening of the respective compartment is adapted to releasably receive a cap of the bag to be accommodated within the metal reinforcement tube.

11. The combination according to claim 10, wherein the outlet opening of the respective compartment is adapted to releasably receive a cap of the bag to be accommodated in the metal reinforcement tube.

12. The combination according to claim 11, wherein the outlet opening of the respective compartment comprises a projection in a longitudinal, radial or longitudinal and radial direction to provide for rotational adjustment of the cap on the metal reinforcement tube.

13. The combination according to claim 1, further comprising a cap, wherein the outlet opening of the metal reinforcement tube is adapted to releasably receive the cap.

14. The combination according to claim 13, wherein the outlet opening of the respective compartment is adapted to releasably receive the cap.

15. The combination according to claim 14, wherein the outlet opening of the respective compartment comprises a projection in a longitudinal, radial or longitudinal and radial direction adapted to provide for rotational adjustment of the cap.

16. The combination accordingly to claim 1, wherein the outlet opening of the metal reinforcement tube has an outlet opening with a diameter smaller than a diameter of the metal reinforcement tube.

17. The combination of claim 1, wherein the first cylindrical body is larger than the second cylindrical body.

18. The combination of claim 1, wherein the first cylindrical body is larger than the second cylindrical body, and each cylindrical body positively engages the metal reinforcement tube molded into the cylindrical body of each compartment.

* * * * *